US008895518B2

(12) United States Patent
Bize et al.

(10) Patent No.: US 8,895,518 B2
(45) Date of Patent: Nov. 25, 2014

(54) COOPERATIVE CONVEYANCE OF BASIC ACTIVE PRINCIPLES BY AMPHIPHILIC ACID MOLECULES

(75) Inventors: Cécile Bize, Toulouse (FR); Muriel Blanzat, Toulouse (FR); Emile Perez, Colomiers (FR); Isabelle Rico-Lattes, Auzielle (FR)

(73) Assignees: Centre National de la Recherche Scientifique, Paris (FR); Universite Paul Sabatier Toulouse III, Toulouse (FR)

( * ) Notice: Subject to any disclaimer, the term of this patent is extended or adjusted under 35 U.S.C. 154(b) by 108 days.

(21) Appl. No.: 13/499,197

(22) PCT Filed: Oct. 4, 2010

(86) PCT No.: PCT/EP2010/064756

§ 371 (c)(1), (2), (4) Date: May 7, 2012

(87) PCT Pub. No.: WO2011/039379

PCT Pub. Date: Apr. 7, 2011

(65) Prior Publication Data

US 2012/0214756 A1 Aug. 23, 2012

(30) Foreign Application Priority Data

Oct. 2, 2009 (FR) ..................................... 09 56893

(51) Int. Cl.

| | |
|---|---|
| ***A61K 31/70*** | (2006.01) |
| ***A61K 47/48*** | (2006.01) |
| ***A61K 47/26*** | (2006.01) |
| ***A61K 9/00*** | (2006.01) |
| ***A61K 31/5415*** | (2006.01) |

(52) U.S. Cl.

CPC ........... *A61K 9/0014* (2013.01); *A61K 47/4803* (2013.01); *A61K 47/26* (2013.01); *A61K 31/5415* (2013.01)

USPC ............................................................ 514/32

(58) Field of Classification Search

None

See application file for complete search history.

(56) References Cited

FOREIGN PATENT DOCUMENTS

FR 2 727 110 A1 5/1996

OTHER PUBLICATIONS

Bize et al. Chem. Commun., 2010, 46, 586-588, published Nov. 17, 2009.*

Bize et al. J Surfact. Deterg (2010) 13:465-473, published Feb. 2010.*

Bize, Associations of New Cationic Amphiphilic and Bolaamphiphiles Sugar Derivatives; Formulations of Bioactives Antihistaminics for Their Administration Skin, Thesis, Oct. 5, 2009.*

Bize, Associations of New Cationic Amphiphilic and Bolaamphiphiles Sugar Derivatives; Formulations of Bioactives Antihistaminics for Their Administration Skin, Thesis, Oct. 5, 2009, machine translation.*

Anderson et al. Arch. Exper. Path. U. Pharmakol., Bd 219, S. 119-129 (1953).*

Kabara et al. Antimicrobial Agents and Chemotherapy, Dec. 1972, p. 492-498.*

Bianchi et al. FEBS Journal 273 (2006) 1115-1123, 2006.*

Asgatay et al., "New polycationic polynorbornene latexes bearing an amphilic sugar corona of counterions: synthesis and complexation with DNA", Collid Polym Sci, vol. 284 (2006) pp. 668-676.

Bize et al., "Physicochemical Studies of the Supramolecular Organization of Catanionic Bolaamphiphilic Associations", Communicaciones Presentadas A las Jornadas de Comite Espagnolde la Detergencia, Barcelona, ES, vol. 38 (2008) pp. 225-234.

International Search Report issued in International Application No. PCT/EP2010/064756 on Nov. 29, 2010.

Preliminary Search Report issued in French Application No. 0956893 on May 28, 2010.

* cited by examiner

*Primary Examiner* — Layla Bland

(74) *Attorney, Agent, or Firm* — Birch, Stewart, Kolasch & Birch, LLP

(57) ABSTRACT

The present invention relates to an intermolecular association complex of an amphiphilic carrier and an active principle G, having the following general formula (I), as well as to the compositions containing same, to the uses thereof, particularly as a drug, and to the method for preparing same.

(I)

S—C(=O)—N(R)—X—$Y^-$ $^+HG$

19 Claims, 1 Drawing Sheet

COOPERATIVE CONVEYANCE OF BASIC ACTIVE PRINCIPLES BY AMPHIPHILIC ACID MOLECULES

The present invention relates to an intermolecular catanionic association of a basic active principle and an acidic surfactant to protect, solubilize and convey the active principle.

Improving the stability of an active principle in order to reduce its adverse effects remains today a very important issue. Generally, this stabilization is carried out both during storage of the active principle by the use of preservatives and antioxidants, and during administration of the active principle by using a carrier to solubilize said active principle and optionally to protect it from degradations due to the immune system and to convey it toward its site of action.

There are today numerous vectorization techniques for active principles. These techniques use various strategies according to the nature of the active principle (hydrophilic or lipophilic), as well as the organ concerned, the dose administered and the duration of administration. For example, the active principle can be encapsulated within a phospholipid vesicle or immobilized in biodegradable polymer microspheres.

Furthermore, the delivery of active principles through the skin has many advantages. The variable rates of absorption and metabolism related to oral treatment are avoided, as well as possible gastrointestinal irritation. Transcutaneous delivery of the active principle also makes it possible to better control its concentration in the blood.

However, the skin has a complex structure and molecules administered transcutaneously or topically must cross a first barrier comprised of the stratum corneum before reaching the bloodstream. The stratum corneum consists of a dense and highly keratinized layer with an average thickness of 10-15 microns. The high degree of keratinization, as well as the compact assembly of cells can constitute a barrier that is virtually impermeable to the passage of an active principle.

For most drugs, the permeabilization rate through the skin, without the addition of a permeabilizing additive, is extremely slow. The effectiveness of cutaneous administration thus rests essentially on the delivery system used which influences the stability of the active principle as well as its bioavailability and its cutaneous biodistribution. The strategies adopted to help a sufficient quantity of active principle penetrate thus generally involve the use of penetration promoters or sophisticated formulations.

Numerous additives can thus be used in order to increase the penetration rate of the active principle through the skin. Most compounds are administered at the same time as the drug (in certain cases the skin can be pretreated with a permeabilization agent) so as to increase the permeability of the stratum corneum and thus increase the penetration of the active principle through the skin. The permeability of many therapeutic agents can be improved by virtue of these permeabilization agents.

Several additives are able to promote the conveyance of active principles through the skin according to various mechanisms of which the most important are as follows:

Extraction of stratum corneum lipids

Disruption of the lipid bilayer structure

Displacement of bound water

Delamination of the stratum corneum

Disruption of the corneal layer

Permeabilization agents can be classified in various categories. For example, solvents such as alcohols, alkyl methyl sulfoxides and polyols increase solubility which increases cutaneous passage. Some solvents such as dimethylsulfoxide (DMSO) or ethanol can extract lipids and make the stratum corneum more permeable. Oleic acid and isopropyl myristate are typical examples of permeabilization agents that disrupt the corneal layer by intercalating themselves in lipid structures. This emollient effect thus increases the diffusion coefficient of the active principle. Also, ionic surfactants and DMSO interact with the keratin of corneocytes, which unfolds the protein structure and increases the diffusion coefficient.

However, most of these delivery systems have the major disadvantage of inducing irreversible changes in the skin.

The present invention describes a novel strategy which consists in making the active principle itself actively participate in its own conveyance, in order to protect, solubilize and convey the drug to its site of action. To that end, we propose to associate by simple acid/base electrostatic interaction a basic active principle with a biocompatible amphiphilic acidic molecule, wherein this association can be further stabilized by hydrophobic interactions between the active principle and the amphiphilic molecule.

In particular, this invention has applications in formulations, in terms of solubilization, protection, conveyance and transcutaneous diffusion of an active principle, wherein the amphiphilic molecule can also play the role of permeabilization agent for transcutaneous conveyance. These formulations, which are simplified and harmless to the skin, thus make it possible to increase the principle active concentration in the skin and to promote its passage through the stratum corneum.

The invention thus proposes to associate a biocompatible amphiphilic acidic transporter with an active principle comprising one or more basic functional groups. This intermolecular association leads to a novel amphiphilic species corresponding to the formation of an acid/base pair bound by electrostatic interactions and stabilized by Van der Waals interactions between the hydrophobic moieties of the two components. The amphiphilic complex thus formed by association can lead, according to its concentration in water as well as the nature of the active principle (volume, hydrophobicity), to a group of self-assembled structures such as micelles or vesicles. The objects thus formed can also be used for self-transport of the active principle.

The present invention thus has as an object an intermolecular association complex of an amphiphilic transporter and an active principle of the following general formula (I):

(I)

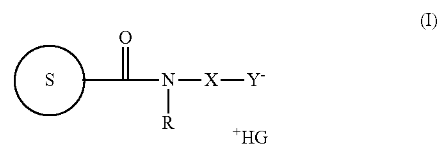

wherein:

S represents a carbohydrate fragment, such as a monosaccharide or a polysaccharide, R represents a hydrogen atom, a $C_1$-$C_{20}$, advantageously $C_1$-$C_{10}$, saturated or unsaturated, linear, branched, cyclic or aromatic hydrocarbon chain, optionally substituted by one or more fluorine atoms, notably perfluorinated, X represents a $C_4$-$C_{10}$ alkyl, alkenyl or alkynyl chain, preferably linear, $Y^-$ represents a carboxylate (—$CO_2^-$), sulfate (—O—$SO_3^-$), sulfonate (—$SO_3^-$), phosphate (—O—P(O)($OR_a$)$O^-$), phosphonate (—O—P(O)$R_b$$O^-$) or phosphinate (—P(O)$R_b$$O^-$) group, with $R_a$ representing a $C_1$-$C_6$ alkyl group and $R_b$ representing a hydrogen atom or a $C_1$-$C_6$ alkyl group, and G represents an active principle comprising at least one primary, secondary or tertiary amine or guanidine (—NH—C(═NH)—$NH_2$) functional group, notably selected from the group comprising antihistaminics, antidepressants, hypotensors, neurotransmitters, amphetamines, anesthetics, antimigraine drugs, cardiac stimulants, nicotinic receptor agonists, vitamins or provitamins, and antineoplastics.

In the context of the present invention, the following terms will be used interchangeably to designate the intermolecular association complexes of an amphiphilic transporter and an active principle of the invention: “complex”, “intermolecular association complex”, “catanionic complex” or “catanionic association.”

In the context of the present invention, “carbohydrate” refers to a monosaccharide or a polysaccharide.

In the context of the present invention, “monosaccharide” refers to an aldose, i.e., a sugar carrying an aldehyde (—CHO) functional group. It can be notably erythrose, threose, ribose, arabinose, xylose, lyxose, allose, altrose, glucose, mannose, gulose, idose, galactose or talose, in D or L form. It is in particular glucose.

In the context of the present invention, “polysaccharide” refers to a chain of at least two monosaccharide units such as defined above. It can be a disaccharide (chain of two monosaccharide units), such as lactose.

In the context of the present invention, “carbohydrate fragment” refers to a carbohydrate fragment lacking its aldehyde functional group.

In the context of the present invention, “alkyl” refers to a saturated linear or branched hydrocarbon chain. When said alkyl chain represents the chain X, it will comprise 4 to 10, preferably 6, carbon atoms and will be advantageously linear. As an example, mention may be made of an n-hexyl chain. When said alkyl chain represents an $R_a$ or $R_b$ group, it will comprise 1 to 6 carbon atoms and can be notably a methyl, ethyl, propyl, isopropyl, butyl, isobutyl, sec-butyl, tert-butyl, pentyl or hexyl group.

In the context of the present invention, “alkenyl” refers to a linear or branched, preferably linear, hydrocarbon chain comprising at least one double bond and comprising 4 to 10, preferably 6, carbon atoms.

In the context of the present invention, “alkynyl” refers to a linear or branched, preferably linear, hydrocarbon chain comprising at least one triple bond and comprising 4 to 10, preferably 6, carbon atoms.

In the context of the present invention, “unsaturated” means that the hydrocarbon chain can comprise one or more unsaturations.

In the context of the present invention, “unsaturation” refers to a double or triple bond between two carbon atoms.

In the context of the present invention, “cyclic hydrocarbon chain” refers to a cyclic hydrocarbon group comprising one or more joined rings, notably 1 or 2 rings. This chain can be saturated or unsaturated and will comprise 3 to 20, preferably 3 to 10, carbon atoms. It can be a cyclopropyl, cyclopentyl or cyclohexyl group.

In the context of the present invention, “aromatic hydrocarbon chain” refers to an aromatic group comprising 6 to 20, preferably 6 to 10, carbon atoms, and comprising one or more joined rings, such as a phenyl or naphthyl group, for example. Advantageously, it is a phenyl.

In the context of the present invention, “perfluorinated” means that all the hydrogen atoms of the hydrocarbon chain have been replaced by fluorine atoms.

These catanionic complexes have the characteristic of self-assembling spontaneously into supramolecular assemblies such as vesicles or micelles, which are thermodynamically stable, which makes it possible to encapsulate the active principle and thus to protect it and to solubilize the assembly by virtue of the hydrophilic S group.

The transporter used in the catanionic association complex of the invention is selected from biocompatible amphiphilic molecules with one or more acidic functional groups.

According to the present invention, the amphiphilic transporter will be selected from carbohydrate derivatives with one or more hydrophobic chains, as well as one or more acidic functional groups capable of interacting electrostatically with the basic active principle.

Said amphiphilic transporter has the following general formula (II):

(II)

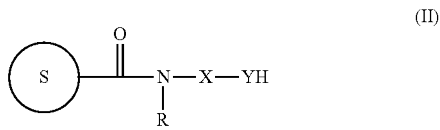

with S, R, X and Y such as defined above. It is thus found in an anionic form in the association complex.

S will more particularly represent a carbohydrate fragment, such as a glucose or lactose fragment.

R will represent notably a hydrogen atom or a $C_1$-$C_6$ alkyl chain, and preferably will represent a hydrogen atom.

Advantageously, X will represent a $C_4$-$C_{10}$, advantageously $C_5$, $C_6$, $C_7$, $C_8$ or $C_9$, and even more advantageously $C_6$, linear alkyl, alkenyl or alkynyl chain. More particularly, X can represent a $C_4$-$C_{10}$, advantageously $C_5$, $C_6$, $C_7$, $C_8$ or $C_9$, and even more advantageously $C_6$, alkyl chain, preferably linear. X can thus represent an n-hexyl chain.

$Y^-$ will represent in particular a $CO_2$ group.

The transporter will thus be advantageously selected from acidic surfactants with sugar head-groups and long chains such as 1,7-glyconamidoheptanoic acids comprising a residue derived from gluconic acid or from lactobionic acid, which will be named Glu6 and Lac6, respectively.

The general formula of 1,7-glyconamidoheptanoic acids Glu6 and Lac6 is as follows:

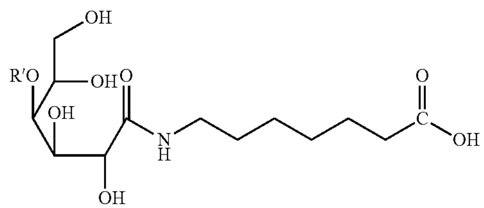

with R'═H for Glu6 and with R'=galactose for Lac6.

These derivatives are prepared according to the prior art described in FR 2 727 110.

The active principle G can be notably an antihistaminic, such as promethazine or mequitazine.

The intermolecular association complex of an amphiphilic transporter and an active principle of the invention can thus be selected from:

Lac6P

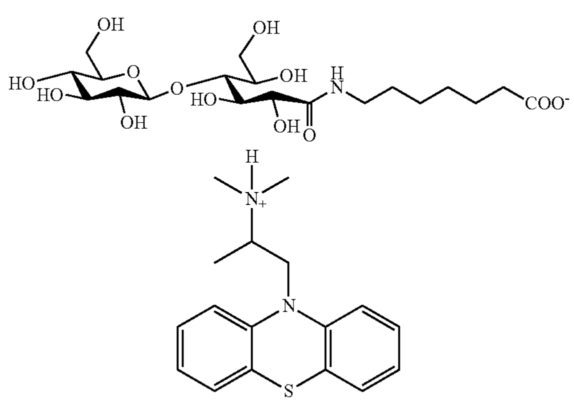

Glu6P

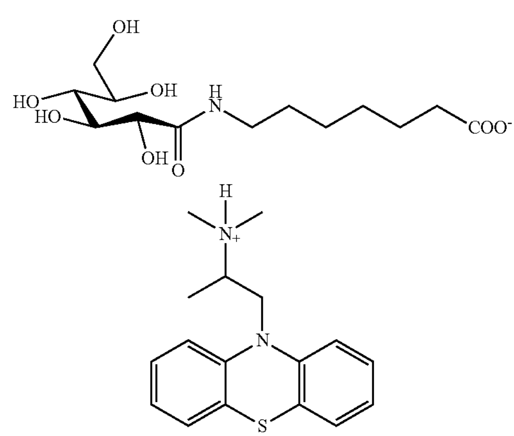

Lac6M

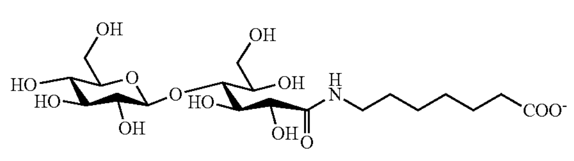

-continued

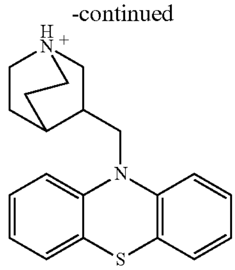

Glu6M

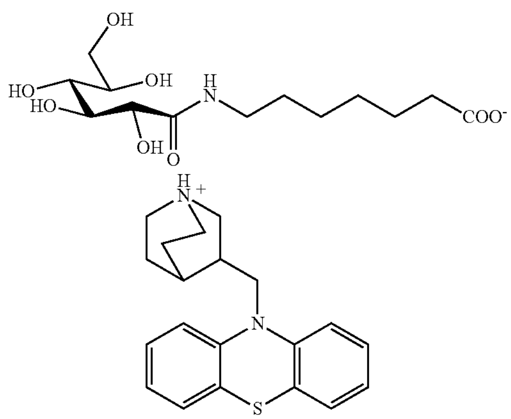

The present invention also has as an object an intermolecular association complex of an amphiphilic transporter and an active principle such as defined above for use as a drug, more particularly as an antihistaminic, antidepressant, hypotensor, neurotransmitter, amphetamine, anesthetic, antimigraine drug, cardiac stimulant, nicotinic receptor agonist, vitamin or provitamin, or antineoplastic, and notably as an antihistaminic.

The invention also relates to the use of an intermolecular association complex of an amphiphilic transporter and an active principle such as defined above for the preparation of a drug, more particularly an antihistaminic, antidepressant, hypotensor, neurotransmitter, amphetamine, anesthetic, antimigraine drug, cardiac stimulant, nicotinic receptor agonist, vitamin or provitamin, or antineoplastic, and notably an antihistaminic.

The present patent application also has as an object a pharmaceutical composition comprising at least one intermolecular association complex of an amphiphilic transporter and an active principle such as defined above.

Said pharmaceutical composition can be more particularly intended for topical or transcutaneous application. It can thus be a hydrogel or an emulsion.

The present invention also has as an object the use of an intermolecular association complex of an amphiphilic transporter and an active principle such as defined above, to protect and/or solubilize and/or convey toward its site of action the active principle G.

The present invention also has as an object a method for preparing an intermolecular association complex of an amphiphilic transporter and an active principle such as defined above, comprising the following successive steps:

- mixing of the amphiphilic transporter of the formula (II) such as defined above and the active principle G such as defined above, and separation of the intermolecular association complex of the amphiphilic transporter and the active principle thus obtained from the reaction medium.

Thus, the intermolecular association complex is formed by simply bringing together the amphiphilic molecule in its acidic form with the active principle in its basic form, in particular in water or another solvent such as methanol. The association complex is thus obtained by an acid/base reaction between the acidic form of the amphiphilic transporter and the basic form of the active principle.

Furthermore, it should be noted that supramolecular structures, such as vesicles or micelles, form spontaneously during the mixing of the transporter and the active principle in aqueous solution, structures that are thermodynamically stable.

The amphiphilic transporter and the active principle will be notably mixed in stoichiometric proportions, i.e., the same number of moles of the amphiphilic transporter and of the active principle are mixed. Furthermore, this mixture can be prepared while heating at a temperature between room temperature and the boiling point of the solvent at atmospheric pressure, and for a period of 1 hour to 72 hours.

The intermolecular association complex thus obtained can then be separated from the reaction medium by filtration, and then optionally freeze-dried.

The present invention will be better understood in the light of the nonrestrictive examples and figures which follow.

FIGURES

EXAMPLES

Example 1

Figure 1:
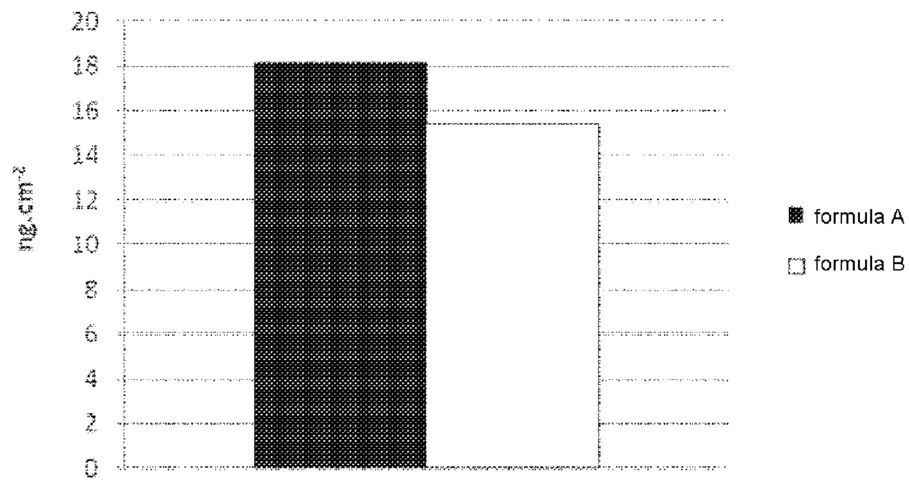
FIG. 1 represents the cumulated quantities of promethazine that diffused through pig skin, after 24 hours, for a formulation A containing free promethazine and a formulation B containing the association Lac6P.

Association Between 1,7-lactobionamidoheptanoic Acid L6 and Promethazine (Lac6P)

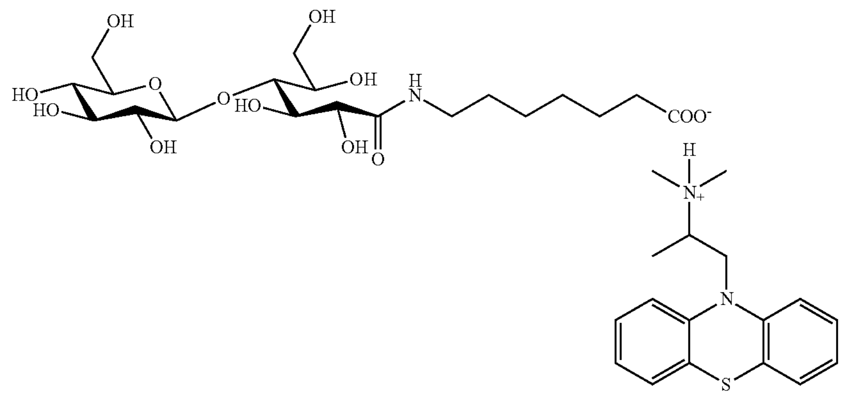

187 mg (0.66 mmol) of promethazine is added to a solution of 320 mg (0.66 mmol) of surfactant derived from the sugar Lac6 in 30 ml of ultrapure water. The round-bottom flask is wrapped with opaque black paper to protect the photosensitive promethazine from light. The reaction mixture is then placed under stirring at 25° C. for 24 hours. A homogeneous solution is then obtained which, after freeze-drying, leads quantitatively to the product in the form of a white powder.

The association constitutes a novel amphiphilic species which forms vesicles in water whose average hydrodynamic diameter is 290 nm (polydispersity index (PI)=0.12) from a critical aggregation concentration (CAC) of $3.3\times10^{-2}$ M.

Example 2

Association Between 1,7-gluconamidoheptanoic Acid G6 and Promethazine (Glu6P)

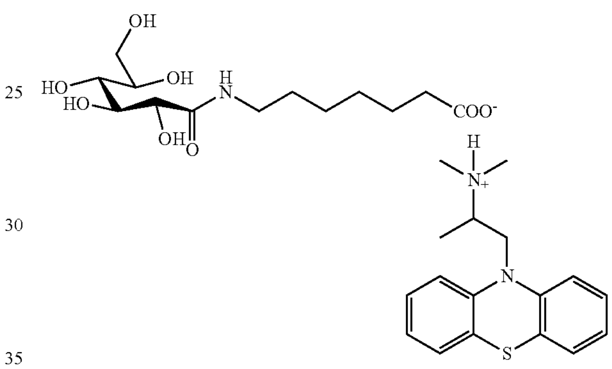

187 mg (0.66 mmol) of promethazine is added to a solution of 213 mg (0.66 mmol) of surfactant derived from the sugar Glu6 in 30 ml of ultrapure water. The round-bottom flask is wrapped with opaque black paper to protect the photosensitive promethazine from light. The reaction mixture is then placed under stirring at 25° C. for 24 hours. A homogeneous solution is then obtained which, after freeze-drying, leads quantitatively to the product in the form of a white powder.

The association constitutes a novel amphiphilic species which forms vesicles in water whose average hydrodynamic diameter is 285 nm (PI=0.10) from a CAC of $1.1\times10^{-2}$ M.

Example 3

Association Between 1,7-lactobionamidoheptanoic Acid L6 and Mequitazine (Lac6M)

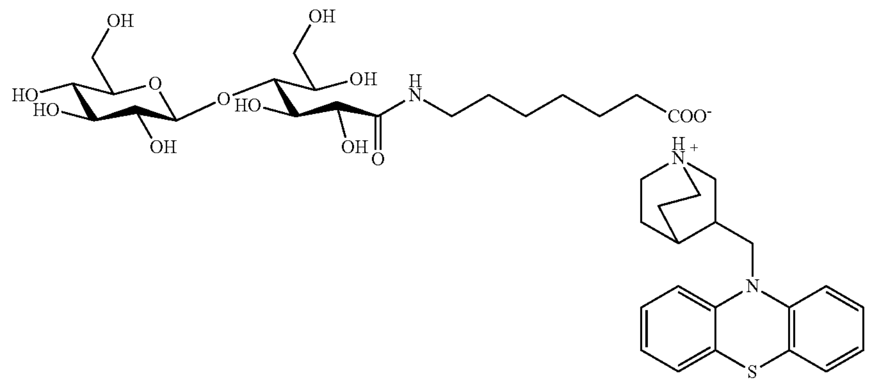

214 mg (0.66 mmol) of mequitazine is added to a solution of 320 mg (0.66 mmol) of surfactant derived from the sugar Lac6 in 30 ml of ultrapure water. The round-bottom flask is wrapped with opaque black paper to protect the photosensitive mequitazine from light. The reaction mixture is then placed under stirring at 25° C. for 24 hours. A homogeneous solution is then obtained which, after freeze-drying, leads quantitatively to the product in the form of a white powder.

The association constitutes a novel amphiphilic species which forms micelles in water from a critical micelle concentration (CMC) of $3.3\times10^{-2}$ M.

Example 4

Association Between 1,7-gluconamidoheptanoic Acid G6 and Mequitazine (Glu6M)

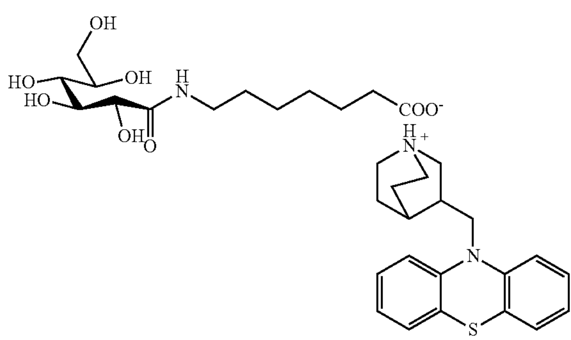

214 mg (0.66 mmol) of mequitazine is added to a solution of 213 mg (0.66 mmol) of surfactant derived from the sugar Glu6 in 30 ml of ultrapure water. The round-bottom flask is wrapped with opaque black paper to protect the photosensitive mequitazine from light. The reaction mixture is then placed under stirring at 25° C. for 24 hours. A homogeneous solution is then obtained which, after freeze-drying, leads quantitatively to the product in the form of a white powder.

The association constitutes a novel amphiphilic species which forms micelles in water from a CMC of $1.1\times10^{-2}$ M.

Example 5

Study of Transcutaneous Penetration Carried Out on Two Associations Prepared with Promethazine and with Lac6P Formulation of the Samples The hydrogels studied are prepared by adding to a 2% by weight Natrosol® aqueous gel, the same volume of a vesicular aqueous solution ($8\times10^{-4}$ M, which is 2% by weight in active principle) of Lac6P or of an aqueous promethazine hydrochloride solution also 2% by weight. Thus, a formulation of 1% by weight Natrosol® and by weight active principle is obtained.

The various formulas tested in this study are as follows:

formula A: preparation of 1% promethazine in a 1% Natrosol® hydrogel, and formula B: preparation of 1% association Lac6P in a 1% Natrosol® hydrogel.

Evaluation of Cutaneous Penetration

Cutaneous penetration of the various formulas was evaluated on 1 $cm^2$ dynamic-flow Franz diffusion cells. The study was carried out ex vivo on pig ear skin with a finite dose over a period of 24 hours.

Skin is taken from pig ears provided by meat processing facilities in Montauban, France. After the ears are cleaned and sheared, skin is taken from the outer portion of the ear and stored at −20° C. For the preparation of the membrane, the pig ear skin is defrosted the day before the study. 500 μm sections are then prepared using a dermatome in order to obtain a homogeneous thickness. Lastly, the sectioned skin is cut into square samples measuring 1.5 cm on each side. The square samples are placed on the diffusion cells with the dermis in contact with the receptor medium. The surface temperature of the skin is maintained at 32° C. by a stream of 37° C. water.

The receptor medium is composed of a solution of 0.9% NaCl and 3% bovine serum albumin (BSA). It is perfused regularly with a flow rate of 1.5 ml/hour.

The formulation to be tested is applied to the surface of a skin sample which separates the donor compartment from the receptor compartment of the diffusion cell. The substances are deposited by double weighing using a 1 ml syringe for the viscous products. Since the study is carried out with a finite dose, the quantity deposited is 5 mg of the formulation. Each formulation is tested on two different cells while one cell is preserved intact to serve as a blank.

The formulation remains in contact with the skin for 24 hours and the receptor medium is sampled at 2, 4, 8, 12, 18 and 24 hours to be analyzed. At the end of the study, the volumes collected are measured. The quantity of antihistaminic in the various fractions is determined by high-performance liquid chromatography (HPLC) assay.

This study was carried out at 25° C. on a Waters 2695 chromatograph equipped with Millipore 510 pumps and an XBridge C18 column (2.1×150 nm, 3.5 μm). The active principles are detected by UV-visible spectrophotometry, at a wavelength of 251 nm, with a Waters 2487 Dual λ Absorbance Detector. Elution is carried out in gradient mode with a flow rate of 0.35 ml/min$^{-1}$. The volumes injected are 10 μl. All the samples were injected three times.

The operating conditions of the selected gradient are as follows:

$t_0$: 94% $H_2O$ 0.1% HCOOH/6% acetonitrile gradient $t_0$ to 15 min: 50% $H_2O$ 0.1% HCOOH/50% acetonitrile gradient 15 min to 16 min: 40% $H_2O$ 0.1% HCOOH/60% acetonitrile gradient The cumulated quantities of promethazine measured by HPLC after 24 hours are presented in FIG. 1.

FIG. 1 thus shows that promethazine in the form of the catanionic complex Lac6P diffuses well through the skin, thus showing that this delivery system, which in all likelihood is less irritating, is suited to topical application.

Example 6

Study of the Photostability of Lac6P and Lac6M in Comparison with Promethazine Hydrochloride and Mequitazine Hydrochloride, Respectively The photostability of the active principle is an important criterion when cutaneous administration is envisaged. Indeed, the presence of a photolabile substance (such as promethazine or mequitazine) within the epidermis in combination with sun exposure can result in activity loss and cutaneous phototoxicity.

The study of the photophysical properties of promethazine hydrochloride and the association Lac6P on the one hand, and mequitazine hydrochloride and the association Lac6M on the other, was thus undertaken by UV spectrophotometry.

This study was carried out on a Hewlett-Packard 8452A diode array spectrophotometer operating at wavelengths between 190 nm and 820 nm.

The solutions were analyzed in quartz cells at concentrations of $4\times10^{-2}$ M and $6.6\times10^{-5}$ M.

Promethazine photodegradation was monitored by HPLC on a Waters 2695 chromatograph equipped with Millipore 510 pumps and an XBridge RP18 column (2.1×100 nm, 3.5 μm). Promethazine is detected by UV-visible spectrophotometry, at a wavelength of 251 nm, with a Waters 2487 Dual λ Absorbance Detector. The mobile phase is composed of a 22/78 mixture of 0.1% formic acid in water and acetonitrile. Elution is carried out in isocratic mode with a flow rate of 0.35 ml/min$^{-1}$. The volumes injected are 10 μl. All the samples were injected three times.

In the case of mequitazine, the mobile phase consists of a 20/70 mixture of 0.1% formic acid in water and acetonitrile.

A calibration curve is prepared beforehand with promethazine hydrochloride over a range of concentrations between $10^5$ M and $5\times10^{-2}$ M.

The photostability of the two antihistaminics in the form of hydrochloride or bioactive catanionic association was thus studied under UV-visible irradiation in order to devalue the influence of self-aggregation on the photochemical properties of the active principles.

To carry out this study, the various solutions ($4\times10^{-2}$ M) are placed in a 25° C. water bath under natural light for several weeks. This gentler mode of irradiation was preferred over the use of a Xenon lamp which degrades the active principle too rapidly and makes it impossible to establish a comparison.

However, before any analysis, several visual observations can be made:

- The promethazine hydrochloride solution turns pink after 24 hours of exposure and changes to blue-violet after a few days. Then, an insoluble compound appears after about two weeks under natural light.
- The vesicular solution of Lac6P turns pink after roughly one week of exposure, and then changes to blue-violet. After about 20 days, the appearance of an aqueous-phase insoluble product, as in the case of the corresponding hydrochloride, is also observed.
- The mequitazine hydrochloride solution turns pink after ten days of exposure, and then changes no further.
- The micellar solution of Lac6M remains colorless and clear for several months.

The late appearance of the pink coloring of the Lac6P solution thus seems to indicate that promethazine degradation is slightly delayed by the self-aggregation of the ion pair. On the other hand, it can be noted that mequitazine degrades only in hydrochloride form.

However, in order to better understand this phenomenon, photodegradation of the hydrochlorides and the associations Lac6P and Lac6M was monitored by visible spectrophotometry. This analysis technique is particularly suited to the study of this phenomenon because it takes color variations into account.

Thus, the various solutions initially have zero absorbance in the visible range. After two months under natural exposure, the appearance of a band for promethazine and mequitazine hydrochlorides, as well as for the catanionic association Lac6P, confirms the color changes observed. It is important to note that in visible spectrophotometry, perceived color is always complementary to absorbed radiation. For example, mequitazine hydrochloride absorbs in the green spectrum (λ=512 nm) and appears pink-purple. Zero absorbance in the visible range for the catanionic association Lac6M is expressed by the absence of color observed after two months under UV radiation. The results obtained are presented in the table below.

| | Promethazine hydrochloride | Mequitazine hydrochloride | Lac6P | Lac6M |
|---|---|---|---|---|
| $\lambda_{max}$ (nm) | 538 | 512 | 562 and 594 | — |

-continued

| | Promethazine hydrochloride | Mequitazine hydrochloride | Lac6P | Lac6M |
|---|---|---|---|---|
| Color observed | violet-indigo | pink-purple | shades of blue | colorless |

These measurements show that the degradation of promethazine is affected by the self-aggregation of the ion pair. The late appearance of pink coloring for the Lac6P solution seems to indicate protection during the first days of exposure. Moreover, promethazine hydrochloride has a band at 538 nm whereas the association Lac6P is characterized by two bands at 562 nm and 594 nm (see table above). These differences seem to demonstrate a different degradation rate for the two compounds.

Containment of the active principle within the membrane of catanionic vesicles thus seems to modify promethazine and mequitazine degradation induced by UV radiation, these active principles thus being protected.

However, the absence of color does not make it possible form conclusions regarding the absence of degradation. The association of mequitazine with the amphiphilic transporter can indeed modify the degradation pathway of the active principle.

In order to refine the results obtained, degradation of promethazine hydrochloride and the catanionic association Lac6P was quantified by high-performance liquid chromatography (HPLC). Degradation is monitored by assaying the quantity of undegraded active principle present in solution (FIG. 2).

Figure 2:
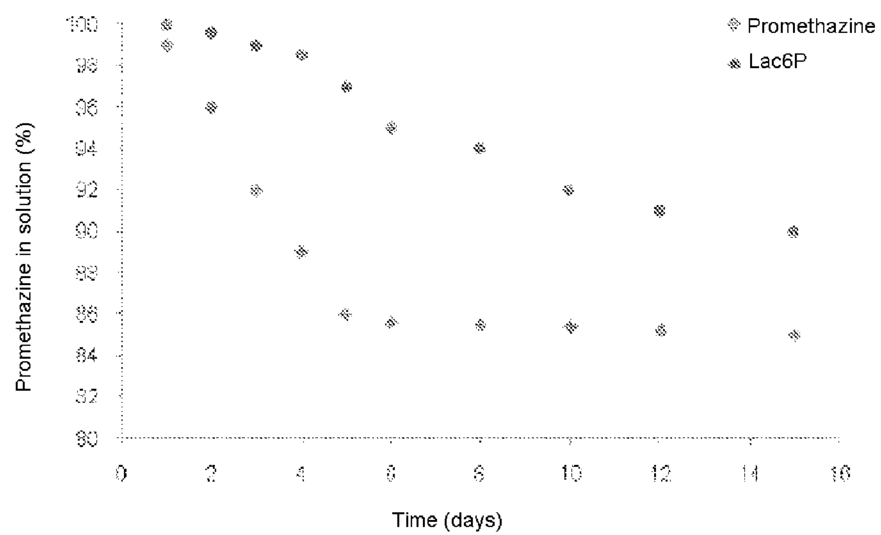
FIG. 2 represents the percentage of undegraded promethazine remaining in solution, as a function of time, for a solution containing promethazine hydrochloride and a solution containing the association Lac6P.

It is thus observed that self-association of promethazine in the form of catanionic vesicles minimizes degradation of the active principle during the first days of exposure (see FIG. 2). After five days under natural light, the association Lac6P and promethazine hydrochloride show a degradation rate of 3% and 13%, respectively. The degradation kinetics is thus delayed by self-organization of the ion pair. The incorporation of promethazine within the membrane of the catanionic vesicles results in significant protection of the antihistaminic during the first days of exposure.

Moreover, it was observed that the catanionic association Lac6M has after two months of exposure a UV spectrum similar to that of undegraded mequitazine hydrochloride. This result reinforces the observations made with visible spectrophotometry. The association of mequitazine with the amphiphilic transporter Lac6 protects, in the long term, the active principle with respect to UV radiation.

The totality of these results thus demonstrates the differences between the degradation of active principles in free or associated forms. In the case of promethazine, degradation kinetics are delayed by self-aggregation, which provides protection of the active principle during the first days of exposure, while in the case of mequitazine, the formation of micelles by the catanionic association Lac6M provides mequitazine significant protection for several months.

Thus, regardless of the type of aggregates formed by the bioactive catanionic assemblies in aqueous solution, the association between the sugar-derived surfactant and the active principle ensures the chemical stability of the latter. This protection phenomenon is particularly advantageous in the development of novel dermo-cosmetic formulations.

The invention claimed is:

1. An intermolecular association complex of an amphiphilic transporter and an active principle of the following general formula (I):

(I)

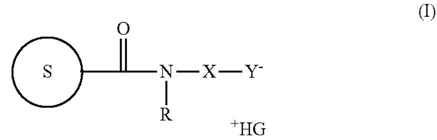

wherein:

S represents a carbohydrate fragment,

R represents a hydrogen atom, a $C_1$-$C_{20}$, saturated or unsaturated, linear, branched, cyclic or aromatic hydrocarbon chain, optionally substituted by one or more fluorine atoms, X represents a $C_4$-$C_9$ alkyl, a $C_4$-$C_9$ alkenyl or a $C_4$ -$C_9$ alkynyl chain, $Y^-$ represents a carboxylate (—$CO_2^-$), sulfate (—O—$SO_3^-$), sulfonate (—$SO_3^-$), phosphate (—O—P(O)($OR_a$)$O^-$), phosphonate (—O—P(O)$R_b O^-$) or phosphinate (—P(O)$R_b O^-$) group, with $R_a$ representing a $C_1$-$C_6$ alkyl group and $R_b$ representing a hydrogen atom or a $C_1$-$C_6$ alkyl group, and G represents an active principle comprising at least one primary, secondary or tertiary amine or guanidine functional group.

2. The intermolecular association complex of an amphiphilic transporter and an active principle of claim 1, wherein S represents a glucose or lactose fragment.

3. The intermolecular association complex of an amphiphilic transporter and an active principle of claim 1, wherein R represents a hydrogen atom or a $C_1$-$C_6$ alkyl chain.

4. The intermolecular association complex of an amphiphilic transporter and an active principle of claim 1, wherein X represents a $C_4$-$C_9$ alkyl chain.

5. The intermolecular association complex of an amphiphilic transporter and an active principle of claim 1, wherein G is an antihistaminic.

6. The intermolecular association complex of an amphiphilic transporter and an active principle of claim 1, selected from:

Lac6P

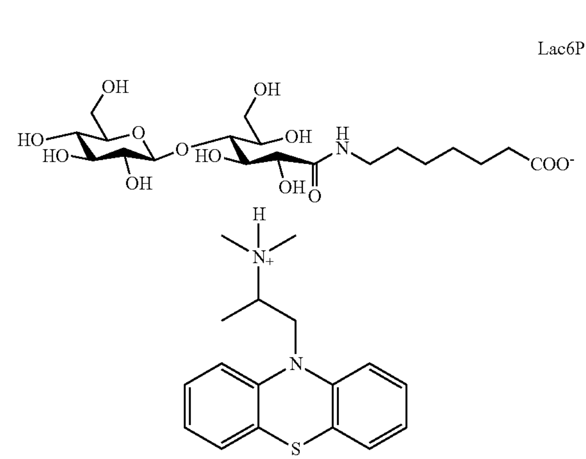

-continued

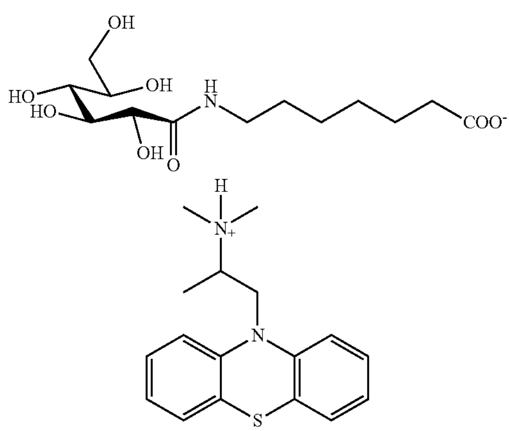

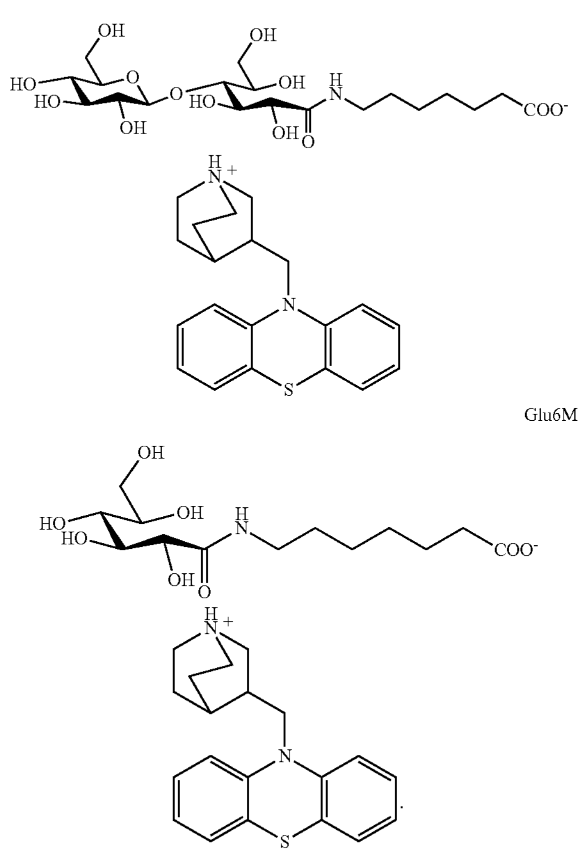

7. The intermolecular association complex of an amphiphilic transporter and an active principle of claim 1, for use as a drug.

8. A pharmaceutical composition comprising at least one intermolecular association complex of an amphiphilic transporter and an active principle of claim 1.

9. The pharmaceutical composition of claim 8, intended for topical or transcutaneous application.

10. The pharmaceutical composition of claim 9, in the form of a hydrogel or an emulsion.

11. A method to protect and/or solubilize and/or convey toward its site of action an active principle G, comprising the step of:

preparing the intermolecular association complex of an amphiphilic transporter and an active principle of claim 1.

12. A method for preparing the intermolecular association complex of an amphiphilic transporter and an active principle of claim 1, comprising the following successive steps:

mixing of the amphiphilic transporter of the following formula (II):

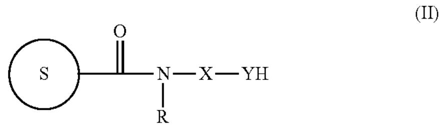

wherein S, R, X and Y are such as defined in claim 1, and the active principle G such as defined in claim 1, and separation of the intermolecular association complex of the amphiphilic transporter and the active principle thus obtained from the reaction medium.

13. The method of claim 12, wherein the amphiphilic transporter and the active principle are mixed in essentially stoichiometric proportions.

14. The method of claim 12, wherein the intermolecular association complex of the amphiphilic transporter and the active principle is separated from the reaction medium by filtration, and then optionally freeze-dried.

15. The intermolecular association complex of an amphiphilic transporter and an active principle of claim 1, wherein S represents a monosaccharide or a polysaccharide fragment.

16. The intermolecular association complex of an amphiphilic transporter and an active principle of claim 1, wherein G represents an active principle comprising at least one primary, secondary or tertiary amine or guanidine functional group, selected from the group consisting of antihistaminics, antidepressants, hypotensors, neurotransmitters, amphetamines, anesthetics, antimigraine drugs, cardiac stimulants, nicotinic receptor agonists, vitamins or provitamins and antineoplastics.

17. The intermolecular association complex of an amphiphilic transporter and an active principle of claim 3, wherein R represents a hydrogen atom.

18. The intermolecular association complex of an amphiphilic transporter and an active principle of claim 4, wherein X represents a n-hexyl group.

19. The intermolecular association complex of an amphiphilic transporter and an active principle of claim 5, wherein G is promethazine or mequitazine.

* * * * *